United States Patent [19]
Nagata et al.

[11] Patent Number: 5,283,365
[45] Date of Patent: Feb. 1, 1994

[54] PROCESS FOR PREPARING HIGH-PURITY ANILINE

[75] Inventors: Teruyuki Nagata; Katsuji Watanabe; Yoshitsugu Kono; Akihiro Tamaki; Takashi Kobayashi, all of Fukuoka, Japan

[73] Assignee: Mitsui Toatsu Chemicals, Incorporated, Tokyo, Japan

[21] Appl. No.: 896,696

[22] Filed: Jun. 10, 1992

Related U.S. Application Data

[63] Continuation of Ser. No. 642,336, Jan. 17, 1991, abandoned.

[30] Foreign Application Priority Data

May 15, 1990 [JP] Japan .................................. 3-123007

[51] Int. Cl.$^5$ ............................................ C07C 209/36
[52] U.S. Cl. .................................................... 564/423
[58] Field of Search ......................................... 564/423

[56] References Cited

U.S. PATENT DOCUMENTS 2,823,235  2/1958  Graham et al. ..................... 564/423

FOREIGN PATENT DOCUMENTS 004750  1/1983  Japan .

Primary Examiner—Richard L. Raymond
Assistant Examiner—Scott C. Rand
Attorney, Agent, or Firm—Millen, White, Zelano & Branigan

[57] ABSTRACT

A process for the continuous preparation of aniline by hydrogenating nitrobenzene is disclosed which comprises the steps of suspending, in an aniline solvent, a catalyst of palladium or palladium-platinum which is deposited on a lipophilic carbon having an oil absorbency of at least 100, adding a zinc compound and an alkali metal carbonate or a zinc compound and an alkali metal bicarbonate as promotors to the reaction system, and carrying out reaction at a temperature of from 150 to 250° C. substantially in the absence of water while aniline and water formed in said reaction are continuously distilled off as vapor from the reaction product, and the concentration of nitrobenzene in the reaction solution is maintained at 0.01% by weight or less.

3 Claims, 2 Drawing Sheets

PROCESS FOR PREPARING HIGH-PURITY ANILINE

This is a continuation of application Ser. No. 07/642,336 filed Jan. 17, 1991 now abandoned.

BACKGROUND OF THE INVENTION (i) Field of the Invention

The present invention relates to a process for preparing aniline by hydrogenating nitrobenzene. Aniline is a very important compound as a basic raw material for urethanes, rubber chemicals, dyes, medicines and the like.

(ii) Description of the Related Art

U.S. Pat. No. 2292879 discloses a process in which an aromatic nitro-compound is hydrogenated in a liquid phase to prepare a corresponding aromatic amine. In this process, a catalyst of nickel, cobalt or copper supported on a finely ground carrier is dispersed in the mixture of an aromatic nitro-compound and an aromatic amine which is the hydrogenation product of the nitro-compound. Hydrogen is then passed through the mixture to carry out reaction. The specification of the U.S. patent describes that the reaction is carried out under conditions of continuously distilling off water formed by the reaction together with the amine from the reaction system, whereby the activity of the catalyst can be maintained at a high level, and that the aromatic amine is used as a reaction solvent in the reaction so as to relatively heighten the concentration of this amine, whereby the activity of the catalyst can be increased.

Japanese Patent Publication No. 50-15779 discloses that in a liquid phase reaction as above-mentioned U.S. patent, the concentration of a produced aromatic amine which is used as a solvent is maintained at 95% by weight or more in the liquid phase, and the reaction is carried out under a pressure as close as possible to atmospheric pressure at a boiling point or a temperature close thereto, so that water produced by the reaction can be easily removed from the system, and that the aromatic amine of the product distilled off from a reactor conveniently contains a less amount of a nitro-compound.

Furthermore, in order to inhibit the production of undesirable impurities which are by-products, it is suggested in the above-mentioned Japanese Patent Publication No. 50-15779 to add an organic base such as an alkanolamine. For example, in the case of the preparation of aniline by hydrogenation of nitrobenzene, triethanolamine is added, but even in this case, condensed aniline which has been distilled off still contains about 0.02% or less of nitrobenzene and about 0.5% or less of impurities having hydrogenated nuclei. It is further described in the above-mentioned publication that in case that triethanolamine is not added, a larger amount of impurities is contained and it is difficult to separate the aniline layer of the condensed aniline product from a water layer. In fact, when the present inventors carried out a tracing test by the use of a diatomaceous earth-nickel catalyst in accordance with the procedure of Example 1 in Japanese Patent Publication No. 50-15779, the condensed aniline which was distilled off contained 0.05% or more of unreacted nitrobenzene and 0.6% or more of compounds having hydrogenated nuclei.

As methods for eliminating these drawbacks, the present inventors have filed two patent applications regarding a process for preparing high-purity aniline which comprises the steps of dispersing, in an aniline solvent, a lipophilic carbon having an oil absorbency of at least 100 on which a catalyst of palladium or palladium-platinum is deposited, and then carrying out reaction at a temperature of from 150 to 250° C. substantially in the absence of water while the concentration of nitrobenzene in the reaction solution is maintained at 0.5% by weight or less and while aniline and water formed in the reaction are continuously distilled out as vapor from a reaction product (Japanese Patent Laid-open No. 57-167946), and regarding a process for continuously preparing high-purity aniline by the catalytic hydrogenation of nitrobenzene which comprises the step of carrying out reaction in the presence of a compound selected from the group consisting of alkali metal hydroxides, alkali metal carbonates, alkali metal bicarbonates, zinc acetate and zinc nitrate while the concentration of nitrobenzene in an aniline reaction solution is maintained at 0.5% by weight or less (Japanese Patent Laid-open No. 58-4750). These methods can provide aniline having a higher purity than a conventional process, but further improvement is desired.

SUMMARY OF THE INVENTION

An object of the present invention is to provide a process for preparing high-purity aniline containing less impurities than the previously suggested two methods in a high productivity.

The present invention is connected with a process for the continuous preparation of aniline by hydrogenating nitrobenzene which comprises the steps of suspending, in an aniline solvent, a catalyst of palladium or palladium-platinum deposited on a lipophilic carbon having an oil absorbency of at least 100, adding a zinc compound and an alkali metal carbonate or a zinc compound and an alkali metal bicarbonate as promotors to the reaction system, and carrying out reaction at a temperature of from 150 to 250° C substantially in the absence of water while aniline and water formed in the reaction are continuously distilled off as vapor from the reaction product, and the concentration of nitrobenzene in the reaction solution is maintained at 0.01% by weight or less.

According to the process of the present invention, the production of substances having hydrogenated nuclei can be inhibited more effectively than the two methods previously suggested by the present inventors, and aniline which is substantially free from unreacted nitrobenzene can be obtained. Thus, high-purity aniline can be prepared in an extremely high productivity. Furthermore, aniline prepared by the process of the present invention can be used, as a raw material, for example, for the manufacture of methylenedianiline (MDA) without any particular additional purification, MDA having high quality being manufactured without allowing unreacted nitrobenzene to accumulate in the system of the MDA manufacturing process.

DETAILED DESCRIPTION OF THE INVENTION

Figure 1:
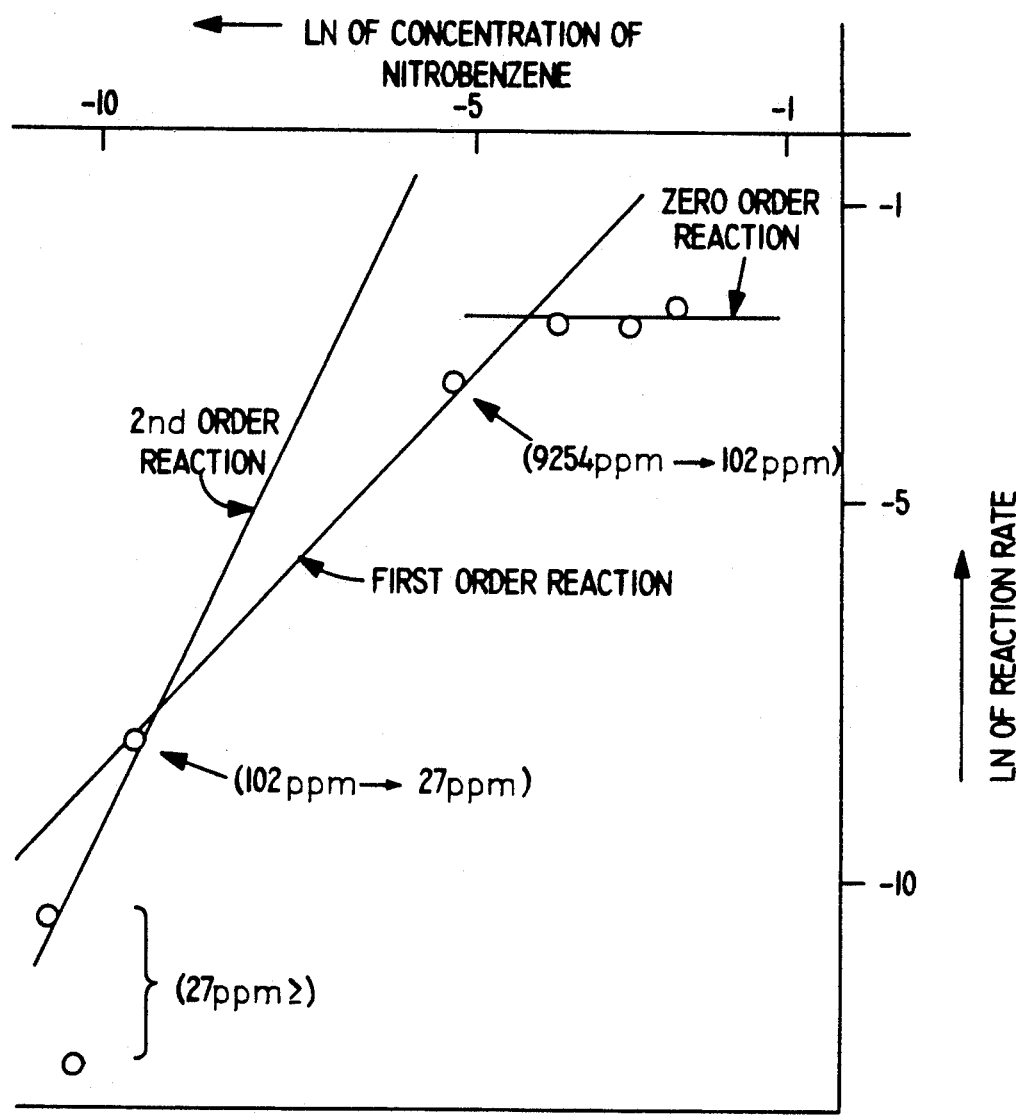
Figure 2:
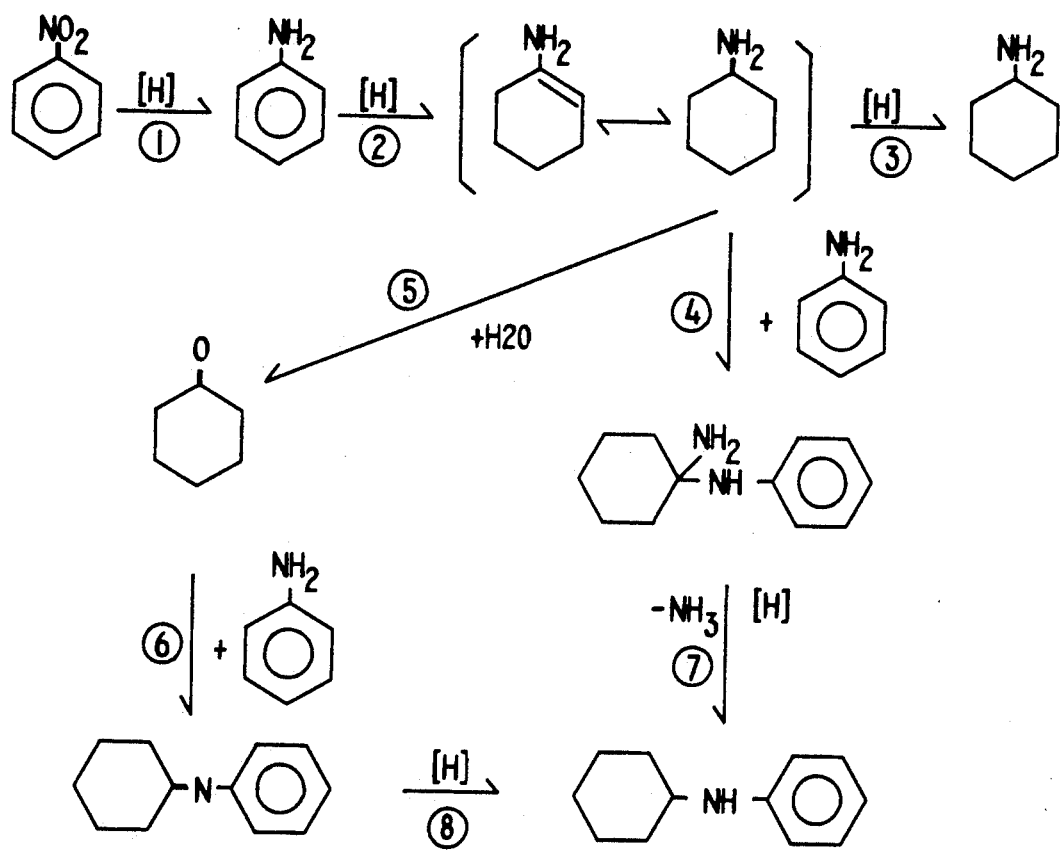

In a process for the continuous preparation of aniline by hydrogenating nitrobenzene wherein aniline is used as a solvent, it is desirable to maintain the concentration of an amine in a reaction solution at a high level, because the content of the unreacted nitrocompound in a product which is distilled off from the reaction system can be lowered. Furthermore, in the case of the reaction involving large exothermic heat as in this reaction, it is generally recommendable that a large amount of a solvent is used to control reaction temperature by using the latent heat of the solvent.

It appears beneficial from the above-mentioned viewpoint to maintain the concentration of the amine in the reaction solution at a level as close as possible to 100% and to lower the concentration of the nitrocompound. However, when the reaction is carried out decreasing the feed of the nitro-compound per unit time so as to lower the concentration of the nitro-compound in the reaction system, the production of the amine per unit time decreases accordingly, with the result that production efficiency deteriorates. A more important point is that under conditions of lowering the concentration of the nitro-compound in an amine solvent, the hydrogenation of an aromatic ring easily occurs as a side reaction, so that impurities are easily formed such as cyclohexylamine, cyclohexanone, cyclohexylideneaniline and cyclohexylaniline. The lower the concentration of the nitrocompound in the reaction system is, the higher the ratio of these by-products is. Therefore, the excessive drop of the concentration of the nitro-compound in the reaction system undesirably leads to the production of aniline containing increased compounds having hydrogenated nuclei. In order to obtain high-purity aniline which can meet the standard for commercial available articles, such complex purification steps as incorporated in a conventional aniline manufacturing process are necessary. Moreover, it has been found that the lower the concentration of the nitro-compound in the reaction system is, the more rapidly the impurities having high boiling points and tar-like substances are accumulated in the reaction solution with the progress of the reaction. These impurities and tar-like substances lower the activity of the catalyst and shorten the life of the same, which makes it difficult to perform the long-term continuous reaction which is economical.

As a means for solving these problems and as a technique for improving the process of Japanese Patent Publication No. 50-15779, the present inventors have developed and disclosed the above-mentioned two methods.

However, as a result of further investigation by the present inventors, it has been found that the proposed two methods are insufficient to achieve the object which is to maintain the quality of distilled aniline at a high level at a nitro-compound concentration of 0.01% by weight or less in the reaction system.

The present invention is directed to a process for preparing aniline by hydrogenating nitrobenzene, and more specifically it is directed to a process which has been developed by additionally improving the above two methods previously proposed by the present inventors.

The present invention is directed to a process for the continuous preparation of aniline by hydrogenating nitrobenzene which comprises the steps of suspending, in an aniline solvent, a catalyst of palladium or palladiumplatinum which is deposited on a lipophilic carbon having an oil absorbency of at least 100, adding a zinc compound and an alkali metal carbonate or a zinc compound and an alkali metal bicarbonate as promotors to the reaction system, and carrying out reaction at a temperature of from 150° to 250° C. substantially in the absence of water while aniline and water formed in the reaction are continuously distilled off as vapor from the reaction product, and the concentration of nitrobenzene in the reaction solution is maintained at 0.01% by weight or less.

The catalyst used in the present invention is a palladium or palladium-platinum catalyst deposited on a porous lipophilic carbon having an oil absorbency of 100 or more. The oil absorbency of this carrier, as defined in Japanese Patent Publication No. 32-9320, is represented by the number of parts by weight of a raw cotton seed oil having an acid value of from 2 to 4 per 100 parts by weight of carbon which can gel. In general, a commercially available catalyst of palladium and/or platinum which is supported on a porous active carbon or alumina as a carrier cannot provide good results in the present invention. The carrier required in the present invention is the lipophilic carbon having an oil absorbency of 100 or more, preferably in the range of from 150 to 300. Moreover, the carrier suitably has a particle diameter of from 20 to 60 mu and a surface area of from to 100 m$^2$/g.

Furthermore, the above-mentioned main catalyst can be prepared by a usual process which comprises precipitating a palladium and/or platinum compound in an aqueous dispersion of the lipophilic carbon carrier, as described in the specification of the aforesaid Japanese publication No. 32-9320. The concentration of palladium or palladium and platinum deposited on the lipophilic carbon is preferably in the range of from 0.1 to 5% by weight, more preferably from 0.5 to 1.0% by weight. Palladium may be used singly, but when palladium is used together with platinum, particularly large effects can be obtained in points of activity and selectivity. In this case, it is desirable that platinum is used in the range of about 5 to 20% by weight with respect to palladium. In addition, as described in the specification of the abovementioned Japanese publication, the carrier may contain a small amount of an oxide or a hydroxide of a metal such as iron or nickel. The concentration of the catalyst in the reaction mixture is usually from 0.2 to 2.0% by weight.

In the present invention, examples of the zinc compound to be added as promotors include zinc oxide, zinc acetate, zinc oxalate and zinc nitrate. Examples of carbonates and bicarbonates of alkali metals include lithium carbonate, sodium carbonate, potassium carbonate, rubidium carbonate, sodium bicarbonate, potassium bicarbonate and cesium bicarbonate. Above all, sodium carbonate and sodium bicarbonate are preferable.

When a hydroxide of an alkali metal was used instead of a carbonate or bicarbonate of an alkali metal, the production of N-cyclohexylaniline was slightly inhibited, but the production of cyclohexylideneaniline increased. With regard to the total amount of the substances having hydrogenated nuclei, no effect was observed.

Organic bases described in the above-mentioned Japanese Patent Publication No. 50-15779 could not exhibit any effect, either, even when used together with the zinc compound.

The amount of the carbonate or bicarbonate of an alkali metal and the zinc compound to be added to the reaction system is usually from 10 to 500 ppm (in terms of the metal), preferably from 20 to 200 ppm. When the amount thereof is less than this range, any effect cannot be perceived, and when it is too much, the main reaction for producing aniline from nitrobenzene is disturbed, so that unreacted nitrobenzene increases. The tendency of this disturbance is more noticeable than in the case of the zinc compound.

In case that the process of the present invention is carried out by the use of the catalyst of the present invention, if water is present in the reaction system, this water causes the activity of the catalyst to decrease and by-products to increase. Therefore, water formed during the reaction is required to be continuously removed from the reaction system, and it is necessary that the reaction is effected in the circumstances substantially free from water. Accordingly, in the process of the present invention, the reaction is carried out by introducing a small amount of nitrobenzene into a reactor through one path, and the introduced nitrobenzene is instantaneously converted into aniline and water and the reaction product is removed in a state of vapor from the system.

This removal of the reaction product can be achieved by evaporating nearly all the reaction product by the use of a part of reaction heat generated at a reaction temperature range of from 150 to 250° C. which can be suitably selected in connection with hydrogen pressure. Afterward, the vapor is condensed, and water is separated from aniline and then removed from the system. At this time, it is desirable, if necessary, that a part of the aniline condensate is returned to the reactor so that the volume of the solution in the reactor may be kept at a substantially constant level during the reaction.

In the present invention, the hydrogenation can be achieved even under atmospheric pressure, but preferably under a pressure of from 1.5 to 10 atm. The performance of the hydrogenation under atmospheric pressure leads to the relative increase of impurities, with the result that the life of the catalyst tends to shorten. Therefore, it is particularly preferred that the hydrogenation is carried out under a pressure of from 3 to 7 atm.

The reaction temperature is in the range of from 150 to 250° C. When the temperature is lower than 150° C., the reaction is too slow and the production per hour is low. In addition, in order to effectively remove water formed during the reaction from the system, a temperature of 150° C. or higher is necessary. However, when the temperature is higher than 250° C., the by-products increase.

In the process of the present invention, the reaction is carried out while the aniline solvent is fed with the raw material nitrobenzene in an amount substantially corresponding to nitrobenzene to be converted into aniline so that the concentration of nitrobenzene in the reaction solution may be maintained at 0.01% by weight or less, preferably 0.005% by weight or less. In case that the reaction is carried out at the nitrobenzene concentration of more than 0.01% by weight (however, less than 0.5% by weight) in the reaction solution, distilled aniline contains about 50 ppm of nitrobenzene and is colorless or light yellow. If this aniline product is directly used as the raw material for the manufacture of methylenedianiline (MDA), the obtained MDA has a slightly yellowish tint, and in case that aniline excessively used at the time of the manufacture of MDA is recovered and recycled, nitrobenzene tends to accumulate in this recycled aniline. Therefore, if the hydrogenation reaction can be performed while the product is kept in the state of high quality and while the concentration of nitrobenzene in the reaction solution is maintained at 0.01% by weight or less, the productivity of aniline can be improved, the thus obtained aniline can provide MDA having extremely high quality, and it is also possible to prevent nitrobenzene from accumulating in the recycled aniline at the manufacture of MDA. It is fair to say that the above-mentioned conception is industrially beneficial.

Now, the present invention will be described in more detail in reference to examples. It is to be noted that these examples are for the elucidation of the present invention and do not intend to limit the scope of the present invention.

EXAMPLE 1

500 g of aniline, 0.25 g of a hydrogenating catalyst obtained by depositing 0.8% by weight of palladium, 0.1% by weight of platinum and 0.8% by weight of iron on carbon powder having an oil absorbency of 260, 0.05 g of zinc acetate and 0.1 g of sodium bicarbonate were placed in a 1-liter stainless steel autoclave equipped with an inlet through which nitrobenzene, the catalyst and a hydrogen gas would be continuously fed, an outlet through which the unreacted hydrogen gas and a product would be removed from a reaction system, a condenser, a stirrer and a thermometer. While an internal temperature and the total pressure were maintained at 190-200° C. and 5 kg/cm$^3$-G, respectively, nitrobenzene, the catalyst, zinc acetate, sodium bicarbonate and hydrogen were fed at rates of 130 g/hr, 0.033 g/hr, 0.005 g/hr, 0.01 g/hr and 90-110 liters/hr, respectively, and formed water and aniline were removed continuously together with the unreacted hydrogen gas in the state of vapor from the reaction system. This vapor was then introduced into the condenser connected to the autoclave and cooled therein, whereby water and aniline were condensed. During this operation, the flow rate of the hydrogen gas was adjusted so as to distill off aniline in an amount corresponding to aniline produced from fed nitrobenzene, i.e., so as to always maintain the weight of a liquid phase mainly comprising aniline in the autoclave at about 500 g. On the other hand, the solution corresponding to the amounts of the catalyst and zinc acetate to be fed (approximately 10% by weight of nitrobenzene to be fed) was drawn out from the reactor every a certain time, in order to maintain the concentrations of the catalyst and zinc acetate at constant levels. The drawn solution was filtered and then analyzed in order to know the concentration of nitrobenzene and amounts of substances having hydrogenated nuclei such as N-cyclohexylaniline and the like and other by-products. The resulting condensate was separated into two layers, thereby obtaining a colorless transparent aniline layer. This aniline layer contained about 4.5% of water. According to the analyzed results by means of gas chromatography and polarography, impurities such as cyclohexanol, cyclohexanone, cyclohexylideneaniline and nitrobenzene were contained in less amounts of 10 ppm or less, 50 ppm or less, 20 ppm or less and 5 ppm or less, respectively, and the purity of aniline was 99.99% or more. During the reaction, the reaction solution in the reactor was discontinuously analyzed and it was confirmed that the concentration of nitrobenzene was kept at 0.01% or less. Therefore, it was not necessary to decrease the feed of nitrobenzene and to increase the feed of the catalyst. In this liquid phase, N-cyclohexylaniline was perceived, but its content was only 0.05% after 9 hours had elapsed since the start of the reaction.

EXAMPLE 2

Reaction was carried out by the use of the same apparatus and the same procedure as in Example 1 except that zinc acetate was replaced with zinc nitrate. In this case, a distilled aniline layer contained, as impurities, 10 ppm or less of cyclohexanol, 70 ppm or less of cyclohexanone, 20 ppm or less of cyclohexylideneaniline and 5 ppm or less of nitrobenzene, and the purity of the aniline was 99.99% or more. Furthermore, during the reaction, the concentration of nitrobenzene in the liquid phase in the reactor was kept at 0.01% or less, and the content of N-cyclohexylaniline was only 0.06% after 9 hours had elapsed since the start of the reaction. Therefore, it was not necessary to decrease the feed of nitrobenzene and/or increase the feed of the catalyst.

COMPARATIVE EXAMPLE 1

Reaction was carried out by the use of the same apparatus and the same procedure as in Example 1 except that zinc acetate was not employed. In this case, a distilled aniline layer contained, as impurities, 200-350 ppm of cyclohexanol, 1300-2200 ppm of cyclohexanone, 70-130 ppm of cyclohexylideneaniline and 20 ppm or less of nitrobenzene, and the purity of the aniline was merely 99.68-99.80%. Furthermore, in the liquid phase in the reactor, N-cyclohexylaniline was formed rapidly and its content reached about 1.7% after 9 hours had elapsed since the start of the reaction, although the content of nitrobenzene in this liquid phase was maintained at 0.01% or less.

EXAMPLES 3 TO 6 AND COMPARATIVE EXAMPLES 2 AND 3

The same procedure as in Example 1 was effected except that kinds and amounts of promotors were changed. The results are set forth in Table 1.

TABLE 1

| | Promotor | | | | | |
| | Alkali Metal Carbonate | | Alkali Metal Bicarbonate | | Zinc Compound | |
| | Kind | Amount (g) | Kind | Amount (g) | Kind | Amount (g) |
|---|---|---|---|---|---|---|
| Example 3 | $Na_2CO_3$ | 0.15 | — | — | zinc acetate | 0.06 |
| Example 4 | $K_2CO_3$ | 0.10 | — | — | zinc nitrate | 0.05 |
| Example 5 | — | — | $NaHCO_3$ | 0.15 | zinc oxide | 0.07 |
| Example 6 | — | — | $LiHCO_3$ | 0.12 | zinc acetate | 0.10 |
| Comp. Ex. 2 | — | — | — | — | zinc acetate | 0.08 |
| Comp. Ex. 3 | NaOH | 0.10 | — | — | zinc acetate | 0.06 |

What is claimed is:

1. In a process for the preparation of aniline by hydrogenating nitrobenzene in an aniline solvent in the presence of a catalyst of palladium or palladium-platinum which is deposited on a lipophilic carbon having an oil absorbency of at least 100; and in the presence as a promoter, of a compound selected from the group consisting of an alkali metal hydroxide, alkali metal carbonate, alkali metal bicarbonate, zinc acetate and zinc nitrate; at a temperature of from 150 to 250° C. at a nitrobenzene concentration in the reaction solution of 0.5% by weight or less, the improvement comprising conducting the hydrogenation continuously and substantially in the absence of water by continuously distilling off aniline and water formed in said reaction as vapor from the reaction product and maintaining the concentration of nitrobenzene in the reaction solution at 0.01% by weight or less, thereby increasing the rate of reaction, and inhibiting the occurrence of side reactions and the formation of byproducts resulting from the low nitrobenzene concentration by employing as the promoter, a zinc compound and an alkali metal carbonate or a zinc compound and an alkali metal bicarbonate.

2. The process for the continuous preparation of aniline according to claim 1 wherein said alkali metal carbonate is sodium carbonate.

3. The process for the continuous preparation of aniline according to claim 1 wherein said alkali metal bicarbonate is sodium bicarbonate.

* * * * *